United States Patent
Harding et al.

(10) Patent No.: US 7,118,747 B2
(45) Date of Patent: Oct. 10, 2006

(54) AT$_4$ RECEPTOR LIGANDS AS ANGIOGENIC, ANTI-ANGIOGENIC, AND ANTI-TUMOR AGENTS

(75) Inventors: Joseph W Harding, Pullman, WA (US); John W Wright, Pullman, WA (US)

(73) Assignees: Pacific Northwest Biotechnology Inc., Pullman, WA (US); Washington State University Research Foundation, Pullman, WA (US)

( * ) Notice: Subject to any disclaimer, the term of this patent is extended or adjusted under 35 U.S.C. 154(b) by 75 days.

(21) Appl. No.: 10/675,470

(22) Filed: Sep. 30, 2003

(65) Prior Publication Data

US 2005/0222044 A1 Oct. 6, 2005

(51) Int. Cl.
*A61K 39/00* (2006.01)
*A61K 38/00* (2006.01)

(52) U.S. Cl. ................. 424/184.1; 424/185.1; 530/316

(58) Field of Classification Search ........... 424/184.1, 424/185.1; 530/316
See application file for complete search history.

(56) References Cited

U.S. PATENT DOCUMENTS 5,219,883 A * 6/1993 Koszyk et al. ............. 514/456

FOREIGN PATENT DOCUMENTS

WO   WO 03/011304A!   * 2/2003

OTHER PUBLICATIONS

Masino, J.A. ("Identification of the Angiotensin IV Receptor Antagonist, Norleual, as a Novel Inhibitor of Angiogenesis and Tumor Growth", Dissertation Abstracts International, May 2003, vol. 64, No. 7B).*

* cited by examiner

*Primary Examiner*—Gary B. Nickol
(74) *Attorney, Agent, or Firm*—Seed IP Law Group PLLC

(57) ABSTRACT

AT$_4$ receptor agonists are potent activators of angiogenesis and can be used to treat diseases that are characterized by vascular insufficiency. AT$_4$ receptor antagonists, which are potent inhibitors of angiogenesis, and can be used as anti-angiogenic agents for the treatment of cancer, diabetic retinopathy, rheumatoid arthritis, psoriasis, atherosclerotic plaque formation, and any disease process that is characterized by excessive, undesired or inappropriate angiogenesis or proliferation of endothelial cells.

24 Claims, 15 Drawing Sheets

(4 of 15 Drawing Sheet(s) Filed in Color)

Table 1. Affinities and lane location of six $AT_4$ novel ligands to rabbit cardiac fibroblast $AT_4$ receptors

| Ligand | $K_i$ (M) | Lane in Figs. 3 |
|---|---|---|
| Nle–Tyr–Ile–hexamide | $1.86 \times 10^{-9}$ | 5 |
| Leu-ψ-Tyr–Leu-ψ-His–Pro–Phe | $1.73 \times 10^{-7}$ | 6 |
| Nle–Tyr–Leu-ψ-His–Pro–Phe | $2.14 \times 10^{-7}$ | 7 |
| Nle–Tyr–Ile–His | $1.42 \times 10^{-6}$ | 8 |
| Nle–Tyr–Ile-$(CH_2)_6$-Phe–amide | $< 10^{-12}$ | 9 |
| Nle–Tyr–Ile–Sar–Sar–dPhe | $1.95 \times 10^{-10}$ | 10 |

ψ = reduced peptide bond [$CH_2$-NH2]

HUVEC

+SA

Control　　　　Treated

A.

B.

A

B

HPF=high power field

SEQUENCE LISTING

```
<160> NUMBER OF SEQ ID NOS: 7

<210> SEQ ID NO 1
<211> LENGTH: 4
<212> TYPE: PRT
<213> ORGANISM: Artificial Sequence
<220> FEATURE:
<223> OTHER INFORMATION: AT4 ligand
<220> FEATURE:
<221> NAME/KEY: MOD_RES
<222> LOCATION: 1
<223> OTHER INFORMATION: Xaa = Nle
<220> FEATURE:
<221> NAME/KEY: MOD_RES
<222> LOCATION: 4
<223> OTHER INFORMATION: Xaa = Acp

<400> SEQUENCE: 1

Xaa Tyr Ile Xaa
 1

<210> SEQ ID NO 2
<211> LENGTH: 6
<212> TYPE: PRT
<213> ORGANISM: Artificial Sequence
<220> FEATURE:
<223> OTHER INFORMATION: AT4 ligand
<220> FEATURE:
<221> NAME/KEY: VARIANT
<222> LOCATION: 1-2
<223> OTHER INFORMATION: Reduced peptide bond
<220> FEATURE:
<221> NAME/KEY: VARIANT
<222> LOCATION: 3-4
<223> OTHER INFORMATION: Reduced peptide bond

<400> SEQUENCE: 2

Leu Tyr Leu His Pro Phe
 1               5

<210> SEQ ID NO 3
<211> LENGTH: 6
<212> TYPE: PRT
<213> ORGANISM: Artificial Sequence
```

```
<220> FEATURE:
<223> OTHER INFORMATION: AT4 ligand
<220> FEATURE:
<221> NAME/KEY: MOD_RES
<222> LOCATION: 1
<223> OTHER INFORMATION: Xaa = Nle
<220> FEATURE:
<221> NAME/KEY: VARIANT
<222> LOCATION: 3-4
<223> OTHER INFORMATION: Reduced peptide bond

<400> SEQUENCE: 3

Xaa Tyr Leu His Pro Phe
 1               5

<210> SEQ ID NO 4
<211> LENGTH: 4
<212> TYPE: PRT
<213> ORGANISM: Artificial Sequence
<220> FEATURE:
<223> OTHER INFORMATION: AT4 ligand
<220> FEATURE:
<221> NAME/KEY: MOD_RES
<222> LOCATION: 1
<223> OTHER INFORMATION: Xaa = Nle

<400> SEQUENCE: 4

Xaa Tyr Ile His
 1

<210> SEQ ID NO 5
<211> LENGTH: 4
<212> TYPE: PRT
<213> ORGANISM: Artificial Sequence
<220> FEATURE:
<223> OTHER INFORMATION: AT4 ligand
<220> FEATURE:
<221> NAME/KEY: MOD_RES
<222> LOCATION: 1
<223> OTHER INFORMATION: Xaa= Nle
<220> FEATURE:
<221> NAME/KEY: MOD_RES
<222> LOCATION: 3
<223> OTHER INFORMATION: (CH2)6
<220> FEATURE:
<221> NAME/KEY: AMIDATION
<222> LOCATION: 4

<400> SEQUENCE: 5

Xaa Tyr Ile Phe
 1

<210> SEQ ID NO 6
<211> LENGTH: 6
<212> TYPE: PRT
<213> ORGANISM: Artificial Sequence
<220> FEATURE:
<223> OTHER INFORMATION: AT4 ligand
<220> FEATURE:
<221> NAME/KEY: MOD_RES
<222> LOCATION: 1
<223> OTHER INFORMATION: Xaa = Nle
<220> FEATURE:
<221> NAME/KEY: MOD_RES
<222> LOCATION: 4,5
<223> OTHER INFORMATION: Xaa = MeGly

<400> SEQUENCE: 6

Xaa Tyr Ile Xaa Xaa Phe
 1               5
```

```
-continued

<210> SEQ ID NO 7
<211> LENGTH: 6
<212> TYPE: PRT
<213> ORGANISM: Artificial Sequence
<220> FEATURE:
<223> OTHER INFORMATION: I-angiotensin IV

<400> SEQUENCE: 7

Val Tyr Ile His Pro Phe
 1               5
```

AT$_4$ RECEPTOR LIGANDS AS ANGIOGENIC, ANTI-ANGIOGENIC, AND ANTI-TUMOR AGENTS

BACKGROUND OF THE INVENTION

1. Field of the Invention

The present invention relates to the general utility of AT$_4$ receptor ligands to alter blood vessel growth (angiogenesis) in diseases associated with insufficient blood supply or those associated with excessive, undesired or inappropriate angiogenesis or proliferation of endothelial cells. In particular, AT$_4$ receptor ligands that inhibit angiogenesis are extremely potent anti-cancer agents that block both the growth of primary tumors and the development of metastatic tumors.

2. Description of Related Art

The dominant therapeutic approaches that are currently employed to treat cancer include surgical removal of primary tumors, tumor irradiation, and parenteral application of anti-mitotic cytotoxic agents. The continued dominance of these long established therapies is mirrored by the lack of improvement in survival rates for most cancers. Improvements that have been observed can be traced not to therapeutic advancements but diagnostic ones. In addition to limited clinical success, devastating side effects accompany classic therapies. Both radiation- and cytotoxic-based therapies result in the destruction of rapidly dividing hematopoietic and intestinal epithelial cells leading to compromised immune function, anemia, and impaired nutrient absorption. Surgical intervention often results in a release of tumor cells into the circulation or lymph systems from which metastatic tumors can subsequently be established. Furthermore, primary tumors often produce or generate endogenous anti-angiogenic substances that suppress the growth of already established but undetected micrometastases (O'Reilly et al., 1994). Their removal, without accompanying treatment that is directed at the micrometastases often leads to rapid expansion of the metastatic tumors with fatal consequences.

Because of the shortcomings of classic treatment regimens several new approaches to cancer therapy have been initiated over the past decade. Most prominent among these are the development of vaccines directed at cancer cells (Morris et al., 2003), the related use of immunotoxins (antibodies linked to cytotoxic agents) (Pastan and Kreitman, 2002), hormone-based therapies (Kenemans and Bosman, 2003), and anti-angiogenics that are designed to limit tumor. growth and metastasis by inhibiting tumor vascularization (Kerbel and Folkman, 2002). Although, the vaccine and immunotoxin therapeutic approach has been under development for some time no immuno-based therapy is now in use as a standard cancer treatment. The utility of this approach is limited by two properties that are inherent to cancer cells. First, cancers are derived from many cell types all with different antigenic profiles. Therefore, each cancer type would necessarily require its own specific set of therapeutic reagents that would entail prohibitively expensive individual development. Second, the antigenic targets of the reagents would never be totally unique to the transformed cancer cells but would also be represented on normal healthy cells resulting in unwanted cytotoxic damage. Hormone-based therapies, while useful for the treatment of a select group of cancers, will never be a treatment option that is generally applicable to the vast majority of cancers that are hormone insensitive. The successful development of a new and generally useful cancer therapy must meet two critical criteria. First, the treatment must target a molecular target or process that is associated with most (if not all) cancers. Next, the treatment must have little or no impact on normal cells. Unlike immune- or hormone-based cancer therapies, anti-angiogenic-based therapies meet both of these criteria.

Neovasularization of tumors is requisite for both the growth and metastasis of tumors. The vascularization of tumor provides it with a dedicated source of nutrients and oxygen that are essential for continued growth. Without a dedicated blood supply the availability of nutrients and oxygen, which must be furnished by vessels external to the neoplasm, is diffusion limited restricting tumor size to about 1 millimeter in diameter. In addition to providing nutrients and oxygen, the tumor vasculature, which is often abnormally permeable, acts as a conduit enabling cancer cells to escape into the general circulation from whence they can establish metastatic tumors at distant sites. The inverse relationship between tumor vascularization and patient prognosis is well recognized and reflects the fact that 90% of cancer patients die of metastatic disease and not primary tumors. The realization that most, if not all, tumors require a dedicated blood supply in order to progress to a clinically relevant state spawned the notion that inhibiting tumor neovasularization could control cancer progression. This could be accomplished by blocking the process of angiogenesis in which vascular endothelial cells divide and migrate to produce branching of established vessels. A particularly attractive aspect of targeting angiogenesis is that the frequency of cancer is increased in older adults who possess quiescent endothelial cells with a normal turnover rate of 1000 days and occurs only during wound healing and menses. Thus, anti-angiogenic drugs meet the primary criteria for a general anti-cancer agent- i.e. broad applicability and minimal effects on normal tissues. Another advantage offered by anti-angiogenic drugs is that they target a cell population (endothelial cells) that is genetically stable and far less likely to support the development of drug resistance that is regularly seen with drugs directed at cancer cells. A final advantage offered by anti-angiogenics is their ready access to endothelial target cells following parenteral application.

SUMMARY OF THE INVENTION

A method of increasing angiogenesis in pathological conditions associated with insufficiencies in vascular perfusion, by producing an AT$_4$ receptor agonist; and administering the AT$_4$ receptor agonist. A method of inhibiting angiogenesis in pathological conditions, where increased angiogenesis and coincidental vascular perfusion are clinically detrimental, by producing an AT$_4$ receptor antagonist; and administering the AT$_4$ receptor antagonist. A method of inhibiting the growth and metastasis of solid tumors, by producing an AT$_4$ receptor antagonist; and administering the AT$_4$ receptor antagonist. A method of inhibiting the growth and metastasis of breast cancer, by producing an AT$_4$ receptor antagonist; and administering the AT$_4$ receptor antagonist.

In any of the above methods the AT$_4$ receptor ligand can be administered locally, intravascularly, intramuscularly, intraperitoneally, subcutaneously, or orally.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1A:
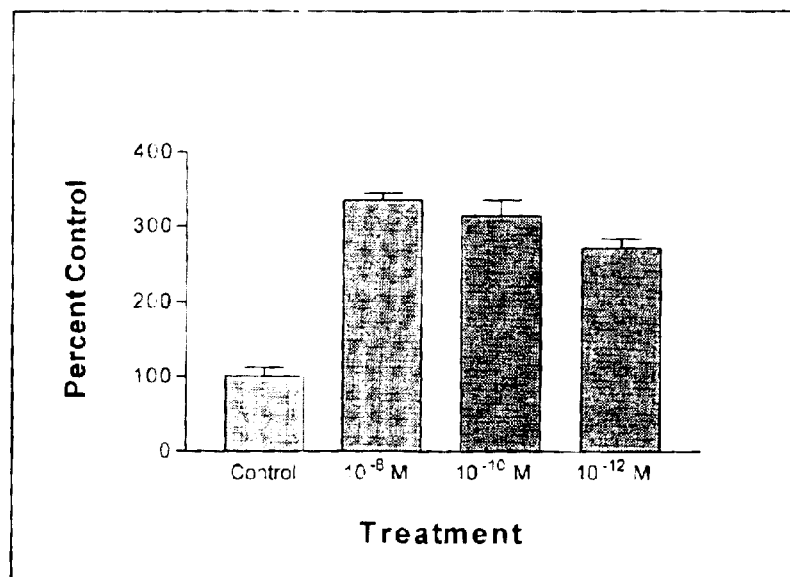
FIGS. 1A and 1B shows the effect of the $AT_4$ receptor agonist, $Nle^1$-AngIV (NORLEU), and the $AT_4$, receptor antagonist, $Nle^1$, Leu-$^3$-$\Psi(CH_2$—$NH_2)^{3\text{-}4}$-Ang IV (NORLEUAL), on the growth of human umbilical vein endothelial cells.

The potential ability of $AT_4$ receptor ligands to alter the angiogenic process was first suggested by the observation that the agonist, $Nle^1$-AngIV can augment the rate of $^3$H-thymidine incorporation in cultured bovine coronary venular endothelial cells (CVEC) (Hall et al., 1995). These initial observations were extended to human endothelial cells (FIG. 1A) where application of the high affinity agonist, $Nle^1$-Ang IV (Sardinia et al., 1994; Wright et al., 1999), produces a dose-dependent increase in growth. Human umbilical vein endothelial cells (HUVEC) were grown in EGM (Clonetics) and 10% calf serum for four days in the absence (control) or presence of $10^{-8}$ M, $10^{-10}$ M, or $10^{-12}$ M $Nle^1$-Ang IV. Cell proliferation was estimated by monitoring mitochondrial activity with the redox-sensitive substrate 3-[4,5-Dimethylthiazol-2-yl]-2,5-diphenyltetrazolium bromide (MTT) (Carmicheal et al., 1987). These data demonstrated that $Nle^1$-Ang IV stimulated endothelial cell proliferation at all doses examined in a dose-dependent manner (Mean+/−SEM, n=6; p<.001) The maximum observed increase was 330% of control levels. These results support the notion that $AT_4$ receptor agonists, like $Nle^1$-Ang IV, can be used to stimulate endothelial cell proliferation and processes like angiogenesis that rely on increased endothelial cell growth.

Figure 1B:
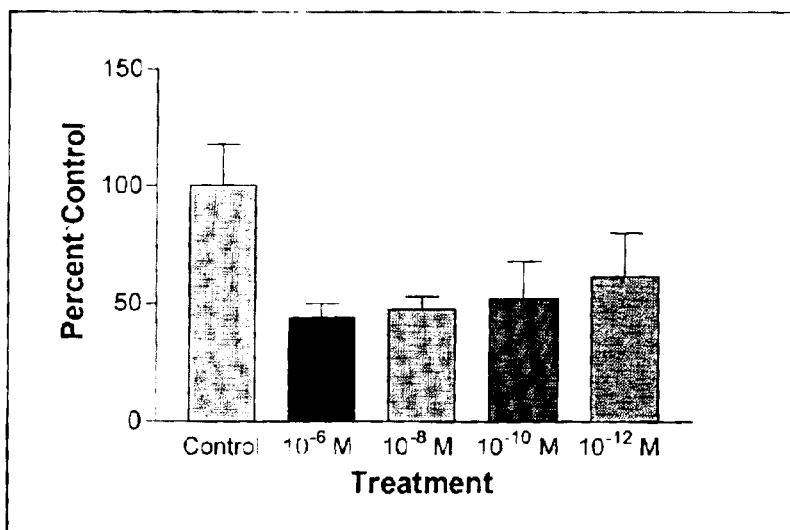

Most relevant for anti-angiogenic cancer treatment is the ability of $AT_4$ antagonists to inhibit endothelial cell growth in culture. Attenuated growth has been observed with both CVECs and with HUVECs (FIG. 1B). After four days of treatment with $10^{-10}$ M $Nle^1$, $Leu^3$-$\Psi(CH_2$—$NH_2)^{3\text{-}4}$-Ang IV (NORLEUAL), a potent $AT_4$ receptor antagonist (Kramar et al., 2001), growth of CVECs was reduced to 25% of control (Mean±SEM; n=8; p<.001). Treatment of HUVECs with NORLEUAL resulted in a dose-dependent inhibition of growth with the largest decease (to 39% control) at $10^{-6}$ M (FIG. 1B). Cell proliferation was again estimated using the MTT assay. Together these data spawned the idea that angiogenesis could potentially be augmented by agonists and inhibited by antagonists of the $AT_4$ receptor.

Figure 2:
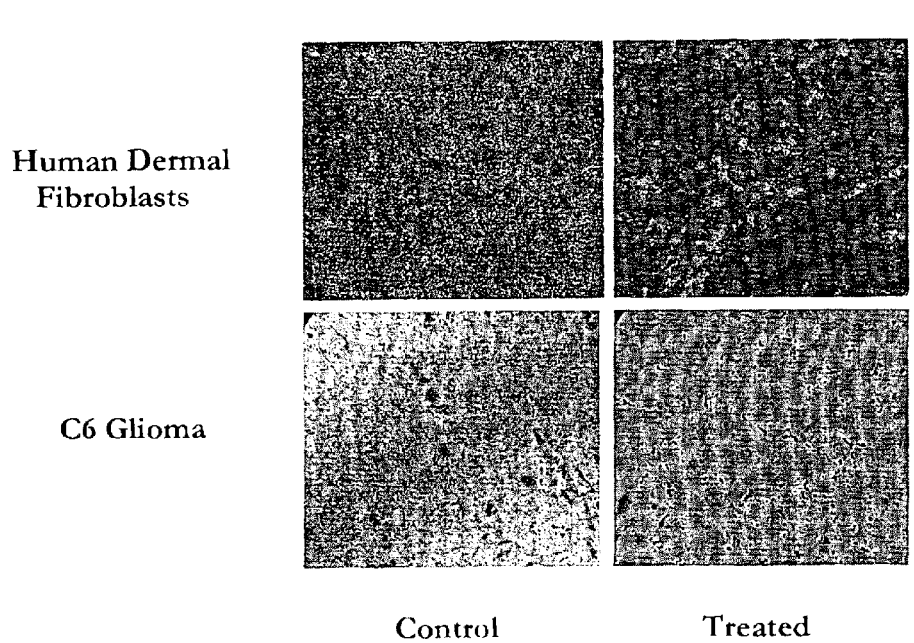
FIG. 2 shows the effect of the $AT_4$ receptor antagonist on the net deposition of extracellular matrix protein by human dermal fibroblasts and C6 glioma cells.
Figure 3:
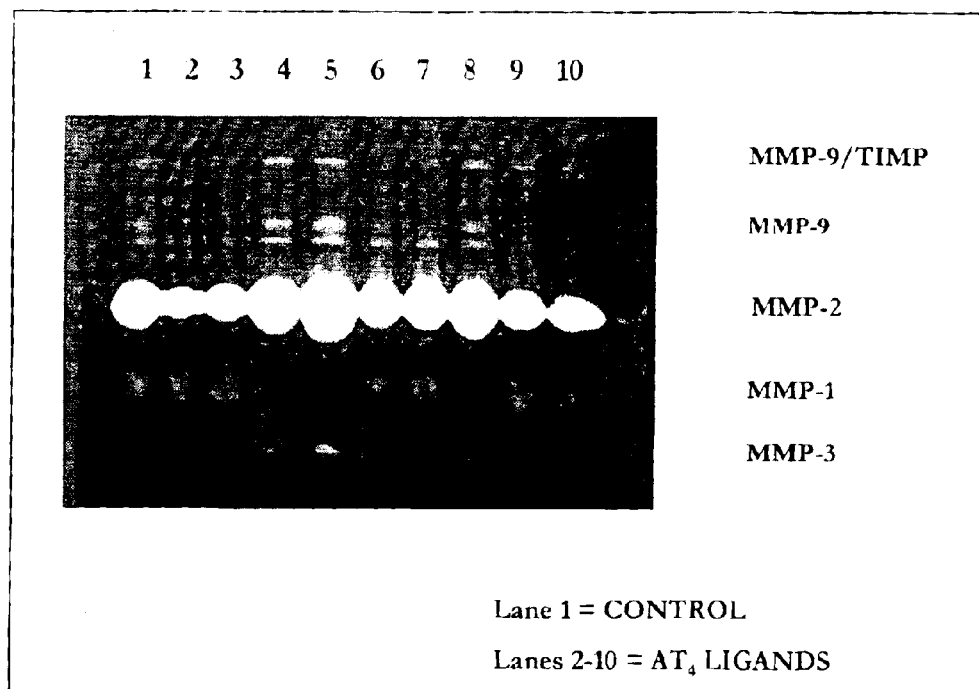
FIG. 3 shows the effect of various AT.sub.4 receptor ligands (SEQ ID NOS: 1–6) on the expression and secretion of matrix metalloproteinases by rabbit cardiac fibroblasts.
Figure 12:
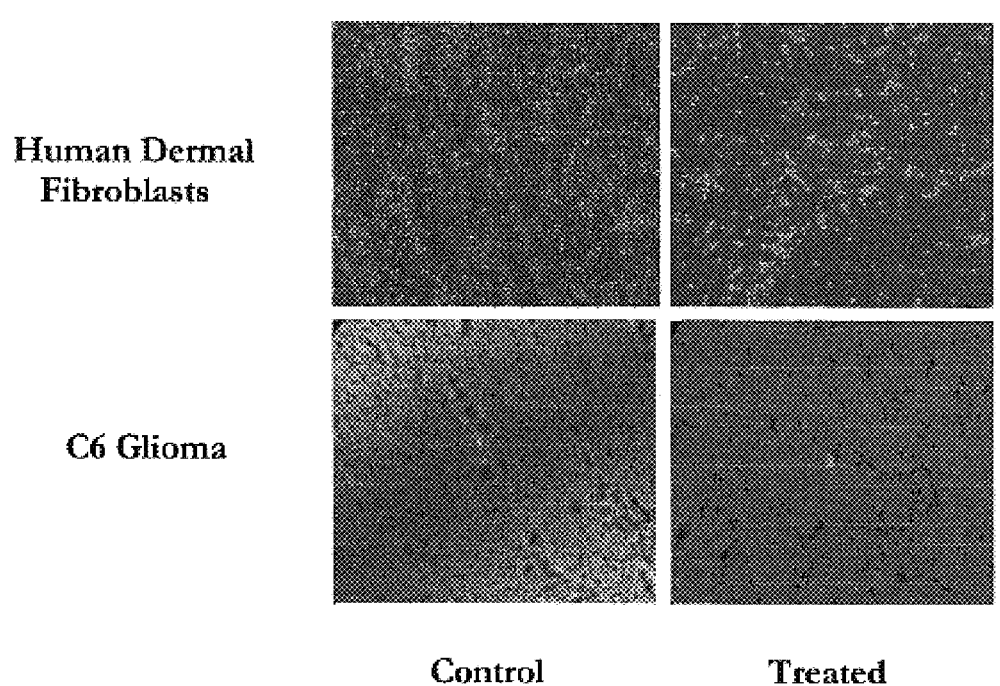
FIG. 12 is color plate showing the effect of the $AT_4$ receptor antagonist, NORLEUAL, on the net deposition of extracellular matrix protein by human dermal fibroblasts and C6 glioma cells.

A second set of observations regarding the function of $AT_4$ receptors indicated that $AT_4$ receptor modulation had a dramatic impact on extracellular matrix (ECM) structure and remodeling. While examining the effect of $AT_4$ receptor ligands on fibroblasts and C6 glioma cells (transformed astrocytes), a near total loss of deposited ECM was observed following antagonist treatment (FIG. 2; FIG. 12[color version]). Human dermal fibroblasts and C6 glioma cells (astrocyte tumor) were treated with $10^{-12}$ M NORLEUAL for 3 days. Cells were stripped with 0.25 % Triton X-100 for 10 minutes and stained with either Coomassie blue (gliomas) or anti-fibronectin (fibroblasts). Stained dots remaining after treatment are nuclei. Although the mechanism responsible for the lose of ECM proteins has yet to be fully elucidated, a contributing factor could be $AT_4$ receptor-dependent alterations in the expression of matrix metalloproteinases. Application of $AT_4$ receptor ligands to rabbit cardiac fibroblasts initiated marked changes in the expression of various matrix metalloproteinases (MMPs) (FIG. 3). The data presented in FIG. 3 is zymographic data. Conditioned media from cardiac fibroblasts treated with various $AT_4$ receptor ligands for 12 hours was loaded and run on a 10% SDS-polyacrylamide gel containing the 1% gelatin, an MMP substrate. After renaturation and activation of MMPs, the gel was incubated at 37° C. for 24 hours to allow for the degradation of gelatin at sites within the gel where MMPs reside. These sites are seen as unstained lytic bands on a background of stained and undegraded gelatin. Lane one is control media from cells with no exposure to $AT_4$ receptor ligands. Lanes 2–4 contained media from cells treated with $Nle^1$-Ang IV, a putative $AT_4$ receptor agonist, at concentrations of 1 nM, 10 nM, and 100 nM respectively. Lanes 5–10 contained media from cells treated with $10^{-6}$ M concentrations of various putative agonists or antagonists (see FIG. 3 and accompanying table for details). These data indicate that $AT_4$ receptor ligands can dramatically alter the expression of several MMPs and suggest that $AT_4$ receptor ligands may be useful for altering MMP expression in pathologies associated with either under or over expression of MMPs.

Figure 4:
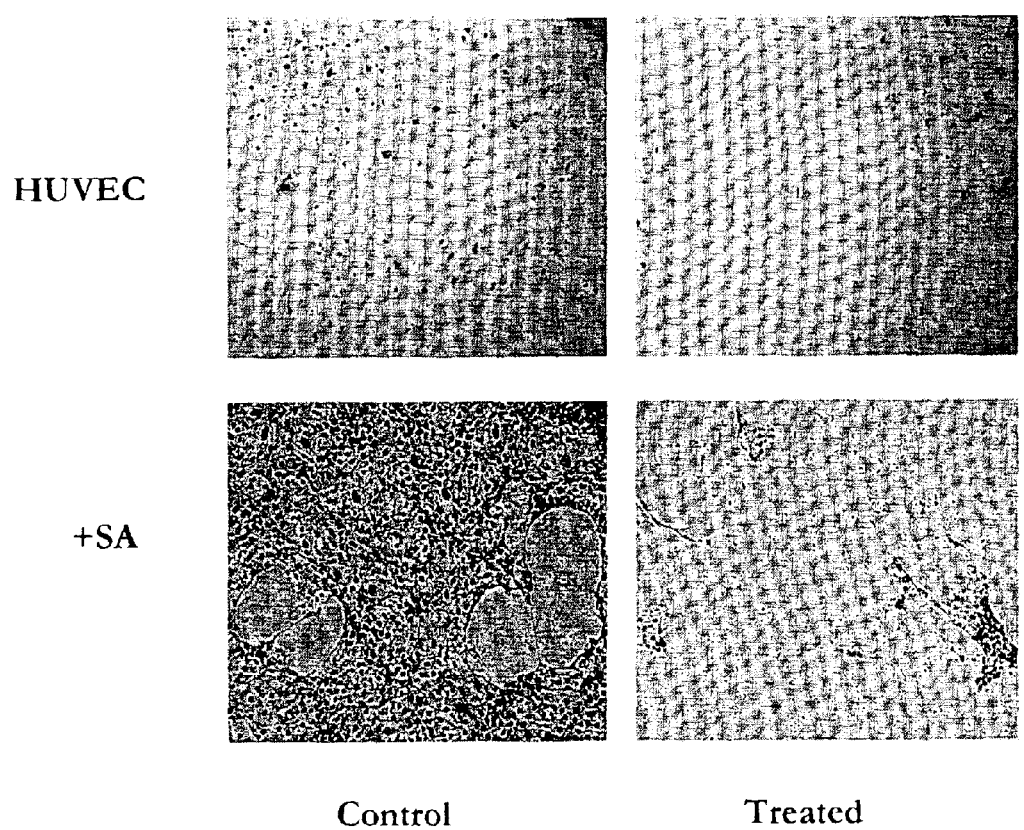
FIG. 4 shows the effect of the $AT_4$ receptor antagonist, NORLEUAL, on the net deposition of extracellular matrix protein by human umbilical vein endothelial cells and +SA-WAZ-2T murine breast cancer cells.
Figure 13:
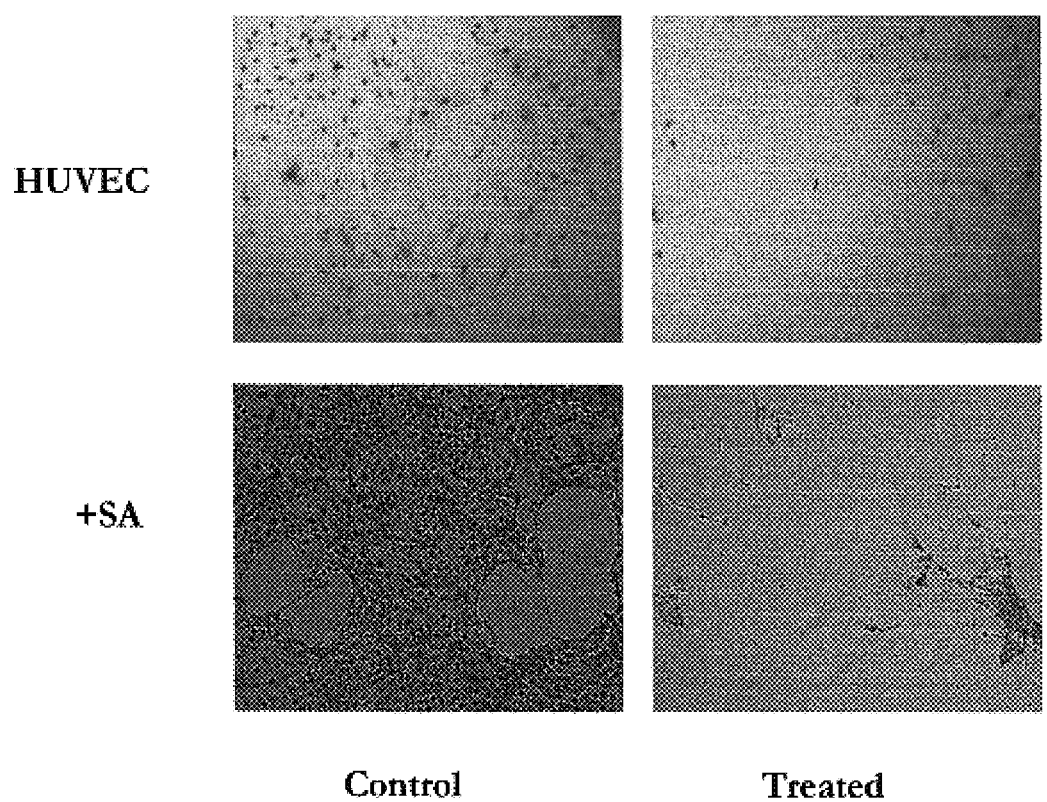
FIG. 13 is a color plate showing the effect of the $AT_4$ receptor antagonist, NORLEUAL, on the net deposition of extracellular matrix protein by human umbilical vein endothelial cells and +SA-WAZ-2T murine breast cancer cells.

The consistent ability of $AT_4$ receptor antagonists to dramatically inhibit the net deposition of ECM protein in various cells (FIG. 2) and the essential involvement of the ECM in mediating endothelial cell growth, motility, and vessel formation made it imperative to assess the impact of $AT_4$ antagonists on endothelial ECM. As seen in FIG. 4 (FIG. 13[color version]), application of the $AT_4$ antagonist NORLEUAL initiates a dramatic reduction in the density of the endothelial-associated ECM. HUVECs and the mouse breast cancer cell line, +SA-WAZ-2T was exposed to the $AT_4$ receptor antagonist NORLEUAL at $10^{-12}$ M for 3 days. Cells were then stripped with 0.25% Triton X-100 and stained with Coomassie blue to visualize total ECM protein. Without an ECM platform endothelial cells fail to migrate and are unable to stabilize new blood vessels.

Figure 5:
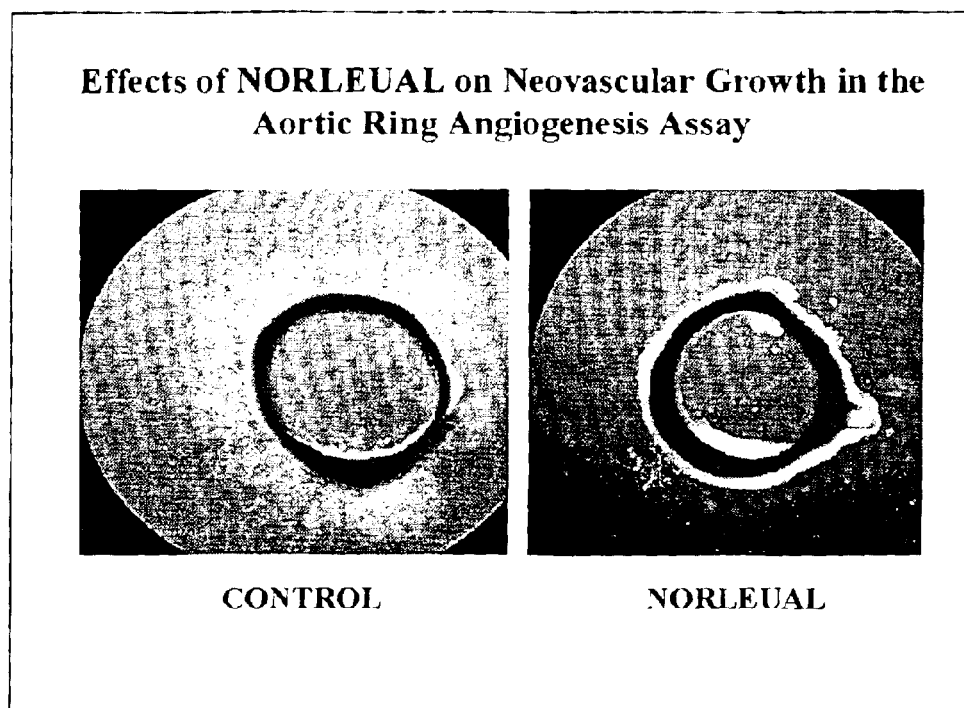
FIG. 5A and 5B show the effect of the $AT_4$ receptor antagonist, NORLEUAL, on the ex vivo development of new blood vessels in the rat aortic ring angiogenesis assay.
Figure 5:
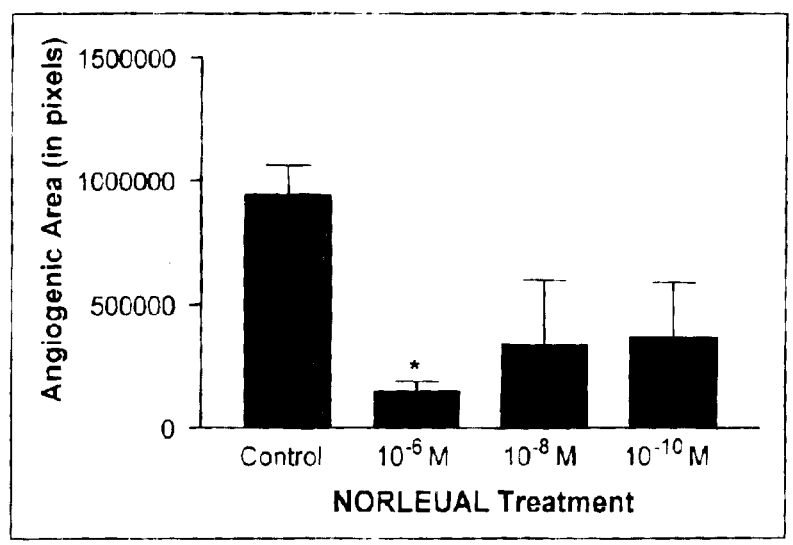
Figure 6:
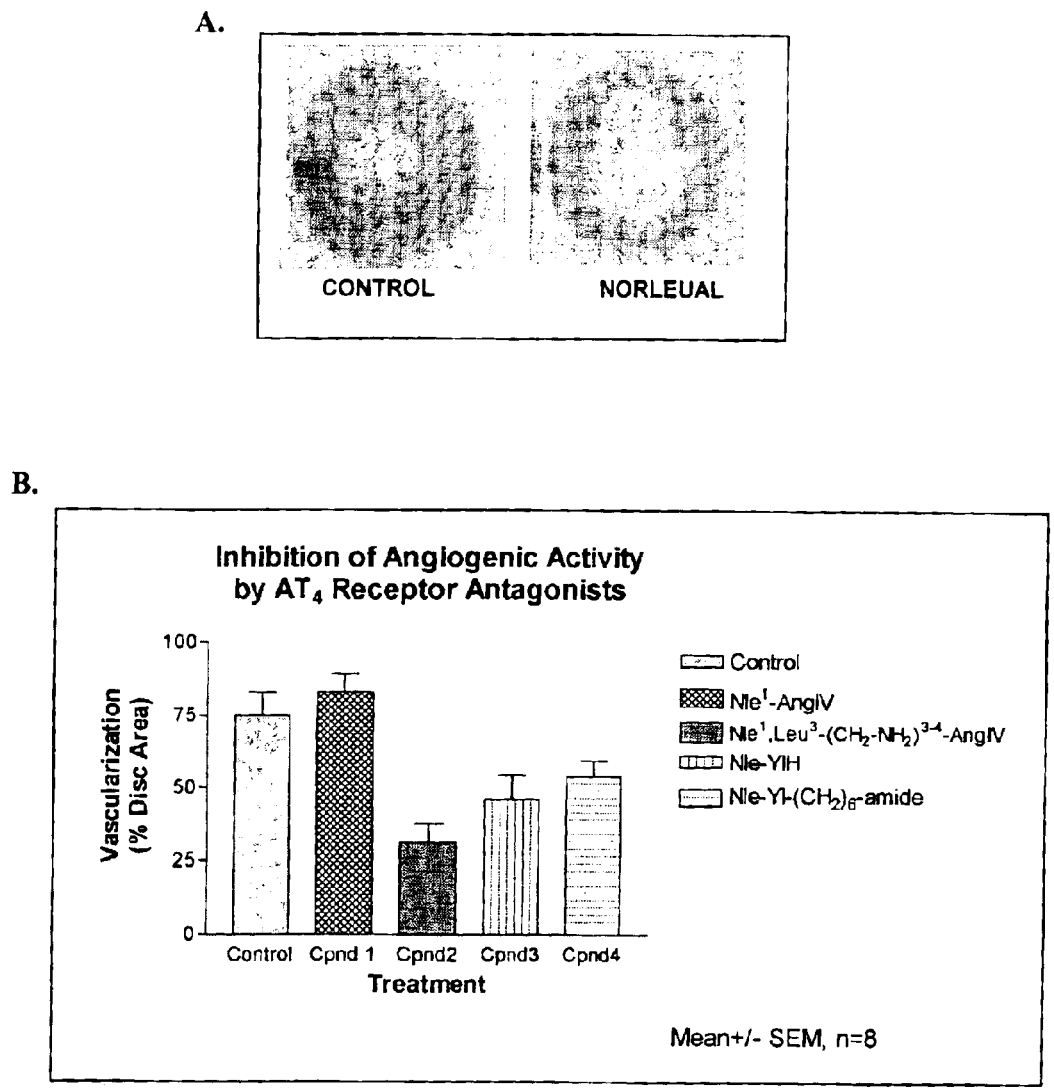
FIGS. 6A and 6B show the effect of various $AT_4$ receptor ligands on in vivo angiogenesis in the rat disc angiogenesis assay.

The ability of $AT_4$ receptor antagonists to inhibit endothelial cell growth and ECM deposition implies that they should exhibit anti-angiogenic activity as well. This prediction has been borne out in studies examining the anti-angiogenic activity of the $AT_4$ receptor antagonist, NORLEUAL, using an ex vivo aortic ring model (FIG. 5) and an in vivo disc angiogenesis assay system in rats (FIG. 6). The data shown in FIG. 5 illustrate the dramatic ability of an $AT_4$ receptor antagonist to inhibit neovascular growth. Rat aortic rings were incubated for 24 hours in a growth factor rich medium (EGM-2) followed by 3 days of incubation in a basal medium (control) or basal media with varying concentrations of NORLEUAL. The data shown in FIG. 5A compare an untreated control ring and a ring treated with $10^{-6}$ M NORLEUAL. FIG. 5B illustrates the dose response effect of NORLEUAL on the inhibition of vessel growth (Mean+/−SEM, n=8; $p<0.02$ for $10^{-6}$ M). These results have been extended to an in vivo model in which growth of new vessels into a subcutaneously implanted disc (sandwich of surgical sponge between impermeable membranes with test compound in the middle) can be quantitated. An example of the type of data that has been generated using the disc angiogenesis assay is shown in FIG. 6A. FIG. 6B shows the results with several $AT_4$ receptor antagonists and the agonist $Nle^1$-AngIV. . Disks (1 cm diameter) composed of surgical sponge sandwiched between impermeable membranes were implanted subcutaneously in the backs of rats. In the center of the disks was a pellet containing the test material. The disks were removed 10 days after implantation, paraffin sectioned, stained with Coomassie blue, and analyzed by quantitative image analysis methods to determine the vascularized area. FIG. 6A shows example control and treated disks that have been stained and sectioned. FIG. 6B shows summary data for several $AT_4$ receptor ligands. Data from discs containing no drug (control), an $AT_4$ receptor agonist (Cpnd 1), or an $AT_4$ receptor antagonist (Cpnds 2–4). Cmpd 2 is NORLEUAL. Each disc contained 10 micrograms of drug. Data is presented as the percent of the total disc area that is vascularized (Mean±SEM; n=8). These data demonstrate the ability of three antagonists (compounds 2–4) to inhibit angiogenesis while the agonist (compound 1) exhibited a trend toward enhancing angiogenesis.

Figure 7:
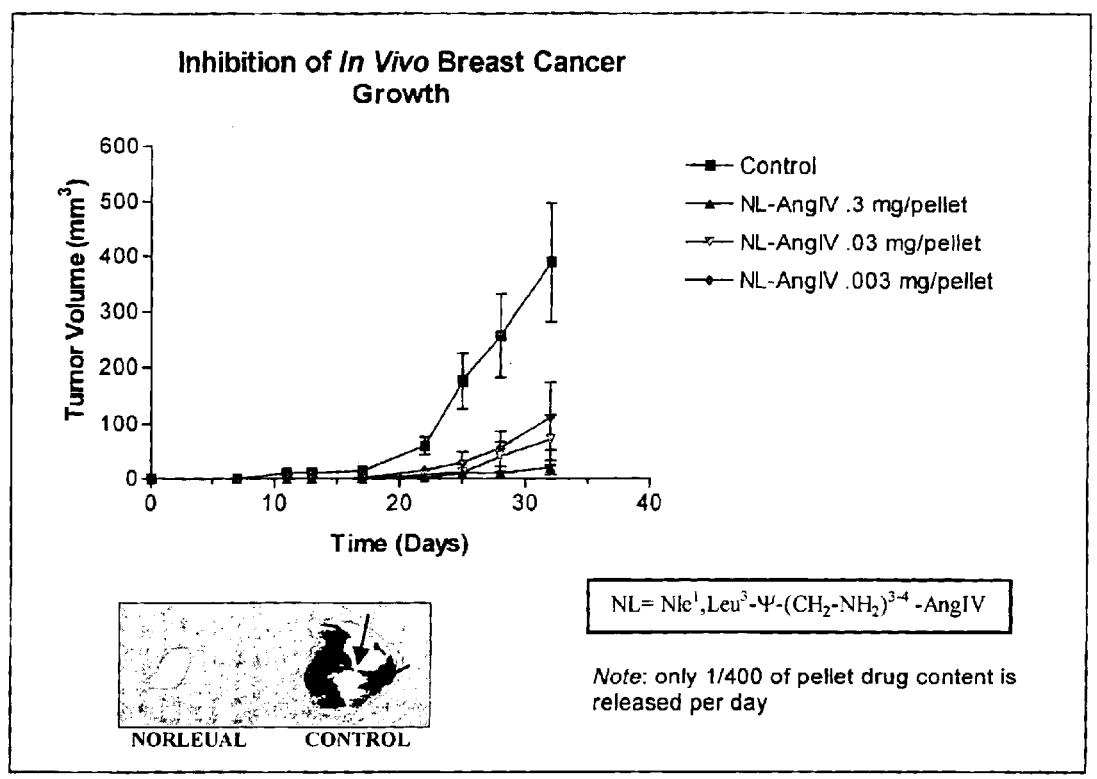
FIGS. 7 shows the inhibitory effect of the $AT_4$ receptor antagonist, NORLEUAL, on the growth of +SA-WAZ-2T murine primary tumors in mice.
Figure 8:
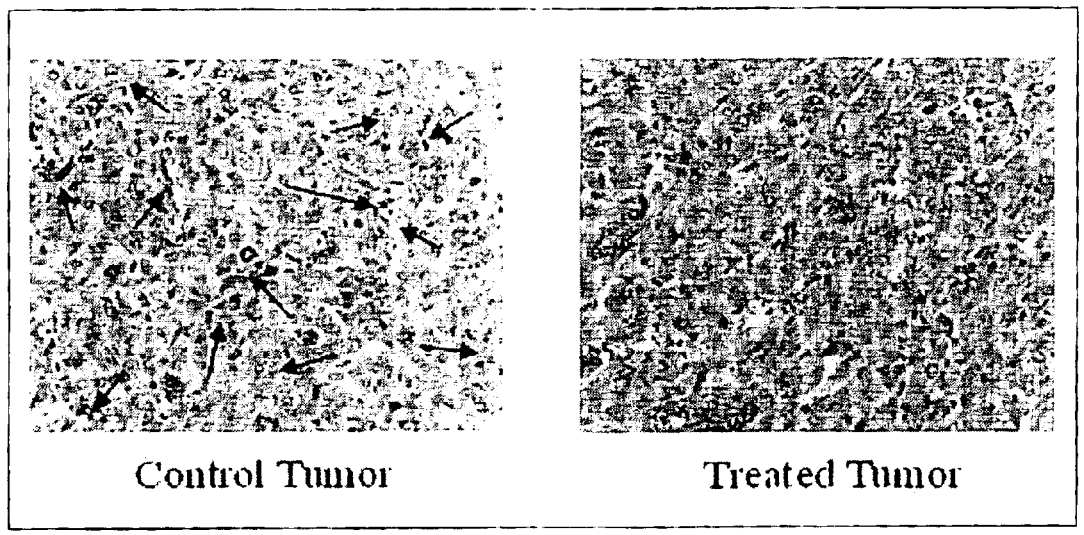
FIGS. 8A and 8B shows the inhibition of tumor angiogenesis in mice following application of the $AT_4$ receptor antagonist, NORLEUAL.
Figure 8:
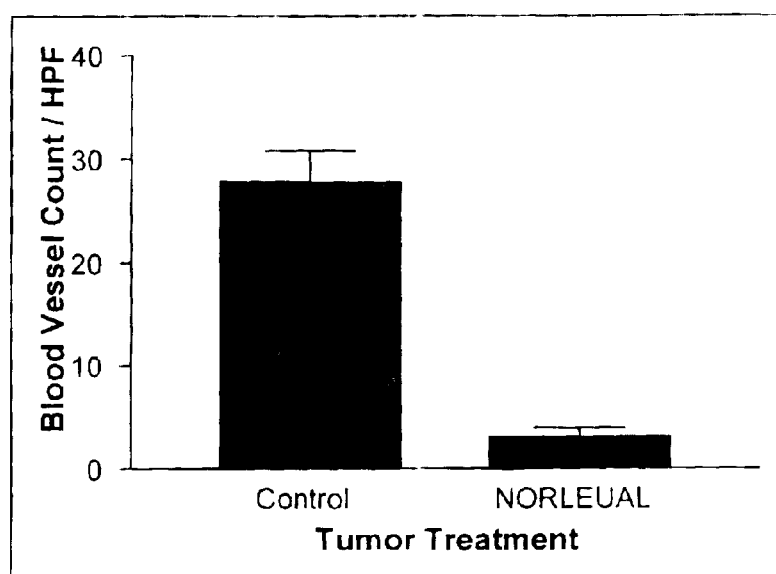
Figure 14:
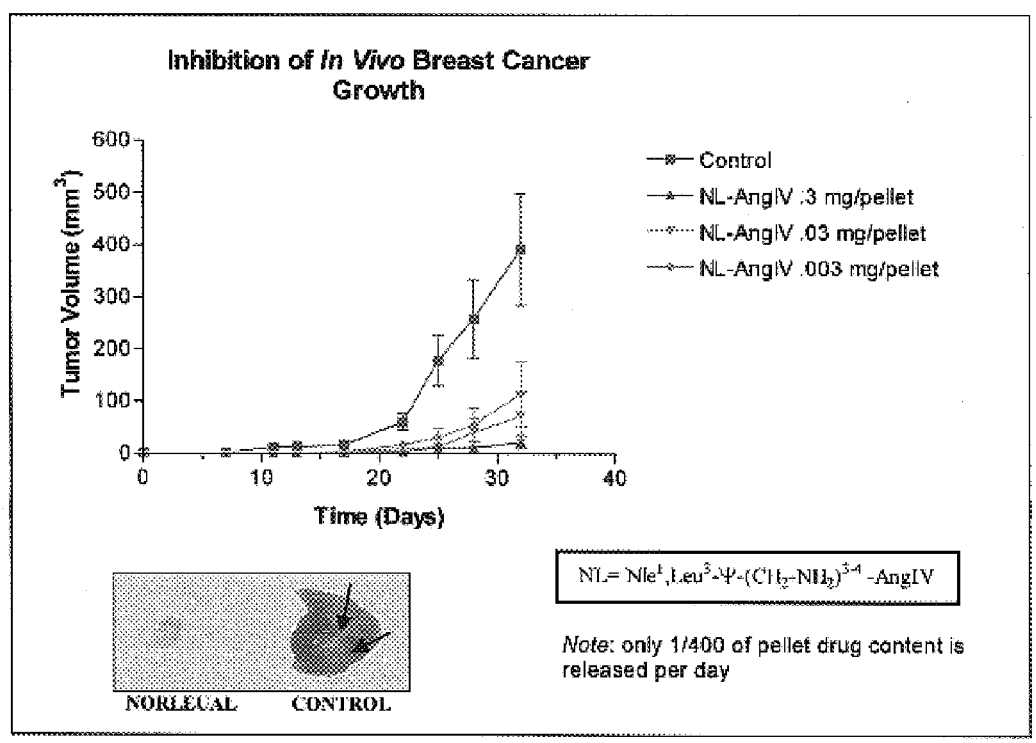
FIG. 14 is a color plate showing the inhibitory effect of the ATreceptor antagonist, NORLEUAL, on the growth of +SA-WAZ-2T murine primary tumors in mice.
Figure 15:
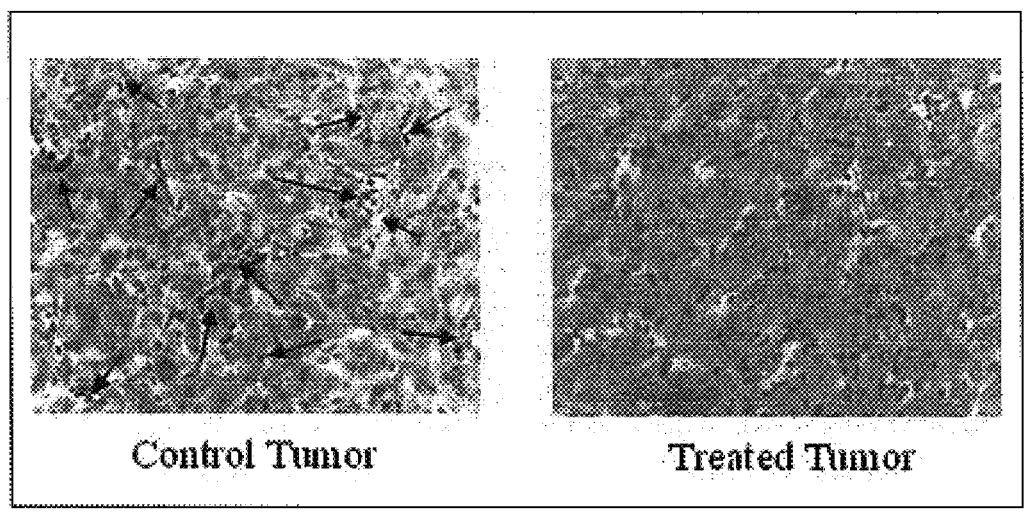
FIG. 15 is a color plate showing the inhibition of tumor angiogenesis in mice following application of the $AT_4$ receptor antagonist, NORLEUAL.

The anti-angiogenic activity of $AT_4$ receptor antagonists predicts that these compounds should also possess anti-tumor activity in vivo. To test this prediction mice were implanted with $5 \times 10^{-5}$+SA-WAZ-2T mouse breast cancer cells (a highly aggressive and metastatic cell line) (Danielson et al., 1980) directly into the mammary gland in the presence or absence of a slow-release pellet containing the $AT_4$ antagonist, NORLEUAL at various concentrations (FIG. 7; FIG. 14[color version]). Mouse mammary glands were injected with $5 \times 10^5$ cells. An Elvax pellet containing an inactive angiokine (control) or NORLEUAL was simultaneously inserted into the gland. Tumors were removed and weighed at various time points. Data shown represents one of three experiments that yielded identical results. The insert shows typical tumors from control and treated mice. Arrows indicate large blood vessels in the control tumor. NORLEUAL dramatically inhibited primary tumor growth as measured by tumor volume. The highest dose examined inhibited growth more than 97%. Equally dramatic as the reduced size of the tumors was their lack of vascularization. This can be seen in FIG. 7 (see insert) and FIG. 8 which shows Factor VIII stained sections of highly vascularized control tumors and treated tumors that were nearly avascular—thus reconfirming that $AT_4$ receptor antagonists inhibit angiogenesis. Tumors were harvested after 5 weeks of drug application and stained for Factor VIII. FIG. 5A (FIG. 15[color version]) shows representative high power fields of sections of control and treated murine mammary tumors. The quantitative data shown in FIG. 8B indicates the number of visible blood vessels in an average high power field. Data are mean+/−SEM, n=6.

Figure 9:
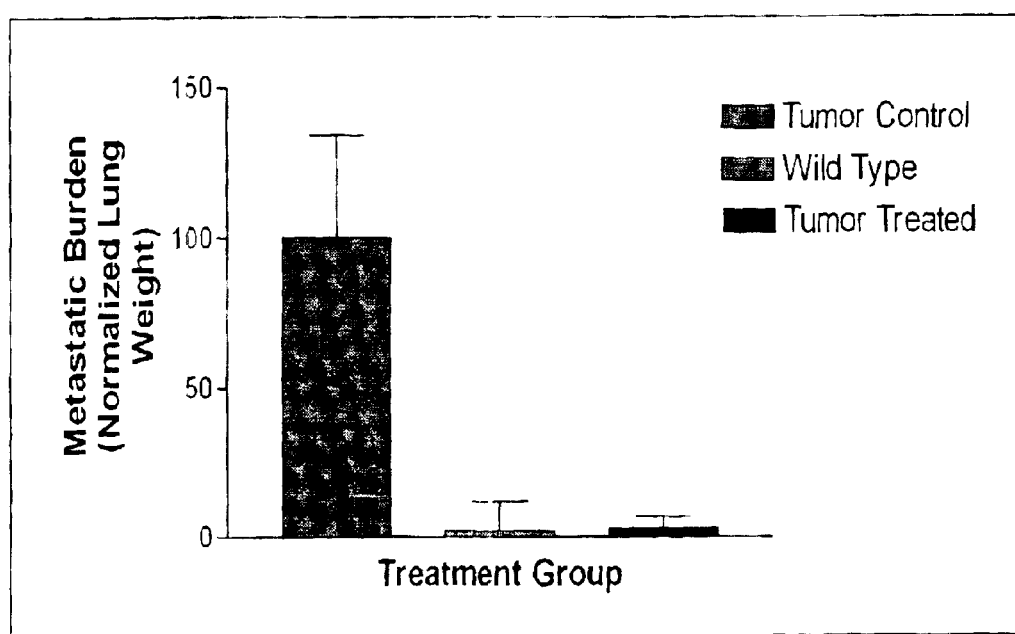
FIG. 9 shows inhibition in the development of lung metastasis in mice following injection of +SA-WAZ-2T cells into the tail vein and subsequent application of the $AT_4$ receptor antagonist, NORLEUAL.

In addition to inhibiting primary tumor growth, $AT_4$ receptor antagonists are also effective at preventing the growth of lung metastases (as assessed by total lung weight and the presence of metastatic tumor nodules) in mice that have had breast cancer cells injected via the tail vein (FIG. 9). In these experiments the drug was applied using Elvax slow-release pellets that were implanted into the gluteus maximus muscle coincident with the injection of tumor cells into the tail vein. Mice were injected with $5 \times 10^5$ murine breast cancer cells and bilaterally implanted with Elvax pellets containing 0.3 mg of NORLEUAL. Lungs were harvested 7 weeks after tumor cell injection and weighed. The results from two combined experiments demonstrated that lungs from treated mice exhibited no gross or microscopic indication of metastases (Mean±SEM. N=8). Visible nodules that were seen in the lungs of control mice were absent from treated mice. Total pulmonary metastatic burden was assessed by comparing lung weights of control and treated mice to naive mice that did not receive any tumor cells. In order to compare just the added lung weight due to tumor infiltration, tumor burden was calculated by subtracting the mean lung weight of wild type untreated controls from the weight of lungs from experimental groups. The mean lung weight of the untreated tumor controls was normalized to 100. Typically, the lung weights of cancer injected, non-treated mice were 50% greater than non-injected controls and treated mice. Spleen weight, another indication of tumor burden, was also normal in treated mice.

Figure 10:
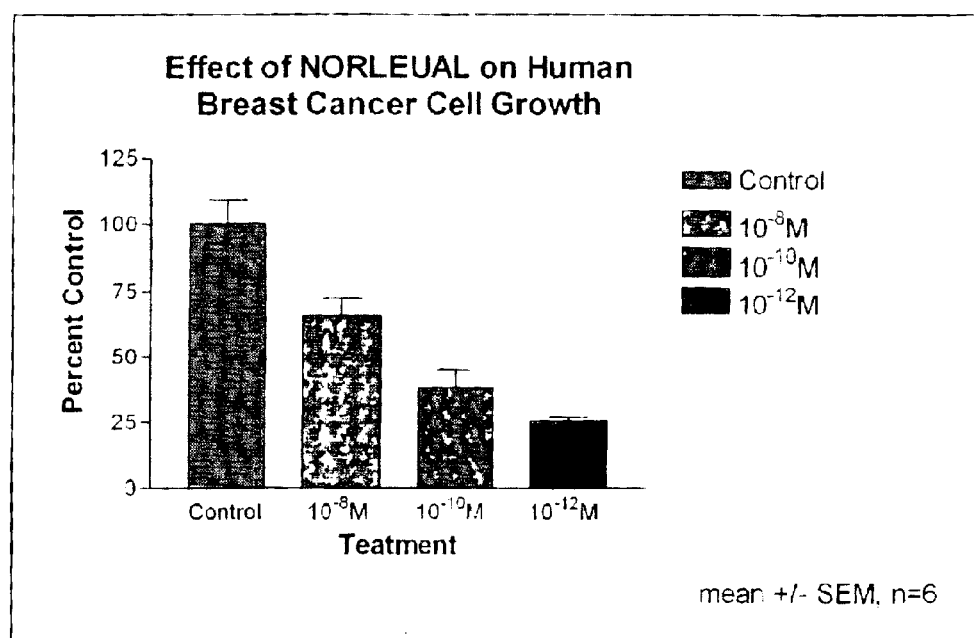
FIG. 10 shows the inhibition of MDA-MB-231 human breast cancer growth by the $AT_4$ receptor antagonist, NORLEUAL.
Figure 11:
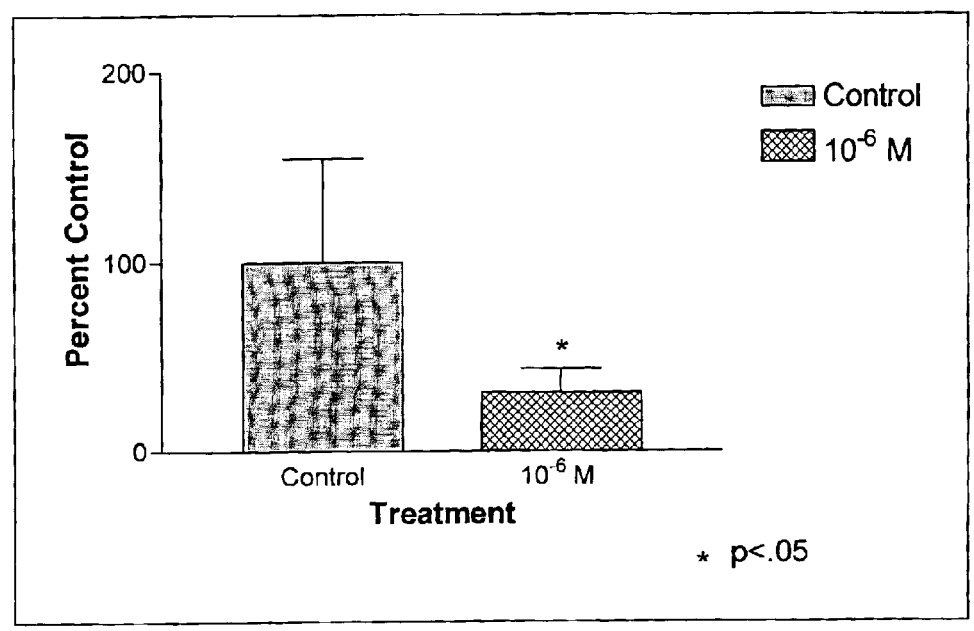
FIG. 11 show the inhibition of DU-145 human prostate cancer growth by the $AT_4$ receptor antagonist, NORLEUAL.

Because of the marked effectiveness of $AT_4$ receptor antagonists to inhibit the growth and metastasis of breast cancer in vivo, and the generally disappointing activity of anti-angiogenic molecules seen in clinical trials (Kerbel and Folkman, 2002), we decided to ascertain whether these drugs might have a direct effect on tumor cells as well as inhibiting angiogenesis. The growth of MDA-MB-23 1 cells, an aggressive estrogen-independent human cell line was inhibited by all concentrations that were examined (FIG. 10). Growth was assessed using the mitochondrial activity dye MTT after four days in culture. Growth was reduced to less than 25% of control by a concentration of NORLEUAL of $10^{-12}$ M (Mean+/−SEM; n=6). Similar results were observed when NORLEUAL was applied at $10^{-6}$ M to DU-145 cells (Mean+/−SEM; n=6), a human prostate cancer cell line (FIG. 11). The unusual reversed dose-response curve seen with the MDA-MB-231 cells may represent differential effects on multiple receptor subtypes with varied ligand affinities. These studies demonstrated that in addition to inhibiting angiogenesis, which indirectly impacts tumor growth and metastatic potential, $AT_4$ receptor antagonists did, in fact, interact directly with tumor cells resulting in a dramatic inhibition of tumor growth in culture (FIG. 10, FIG. 11), a near total loss of secreted ECM proteins (FIG. 4), and alterations in the expression of matrix metalloproteinases (data not shown). The ability of $AT_4$ receptor antagonists to inhibit both the angiogenic process as well as the proliferation of human cancer cells makes them unique among anti-cancer agents and provides a plausible explanation for their dramatic ability to inhibit tumor growth and metastasis.

Definition: An $AT.sub.4$ receptor ligand is defined as any molecule that can compete for the binding of $^{125}I$-angiotensin IV (VYIHPF) (SEQ ID NO: 7) to plasma membranes from bovine adrenal glands, which are enriched in $AT_4$ receptors, with a $K_1 <$ or $= 10^{-7}$ M.

It is to be understood that the above-described arrangements are only illustrative of the application of the principles of the present invention. Alternative arrangements may be devised by those skilled in the art without departing from the spirit and the scope of the present invention. The appended claims are intended to cover such modifications and arrangements. Thus, while the present invention has been shown in the drawings and fully described above with particularity and detail in connection with what is presently deemed to be the most practical and preferred embodiments of the invention, it will be apparent to those of ordinary skill in the art that numerous modifications, including but not limited to the application of the present invention to treat: lung cancer, prostrate cancer, ovarian cancer, gastrointestinal cancers, melanoma or to treat nonsolid tumors such as leukemia, Hodgkin's disease, multiple myeloma, other hematopoietic-based cancers. $AT_4$ receptor agonists are potent activators of angiogenesis and can be used to treat diseases that are characterized by vascular insufficiency. In the alternative, $AT_4$ receptor antagonists, which are potent inhibitors of angiogenesis, and can be used as anti-angiogenic agents for the treatment of cancer, diabetic retinopathy, rheumatoid arthritis, psoriasis, atherosclerotic plaque formation, and any disease process that is characterized by excessive, undesired or inappropriate angiogenesis or proliferation of endothelial cells, may be performed without departing from the principles and concepts set forth herein.

What is claimed is:

1. A method of inhibiting angiogenesis in pathological conditions where increased angiogenesis and coincidental vascular perfusion are clinically detrimental, comprising the steps of: producing an $AT_4$ receptor ligand, having a structure selected form the group consisting of $NH_3^+$-norleucine-tyrosine-isoleucine-histidine-$COO^-$(SEQ ID NO: 4), and norleucine-tyrosine-isoleucine-(6-amino-hexanoic acid)-$CONH_2$SEQ ID NO: 1); and administering the $AT_4$ receptor ligand.

2. A method of inihibiting angiogenesis in pathological conditions where increased angiogenesis and coincidental vascular perfusion are clinically detrimental, comprising the steps of: producing an $AT_4$ receptor ligand having a structure of: norleucine-tyrosine-lucine-$\Psi$-$(CH_2$-$NH_2)^{3-4}$-histidine-proline-phenylalanine-$COO^-$(SEQ ID NO 3; and administering the $AT_4$ receptor ligand.

3. The method of inhibiting angiogenesis according to claim 1 or claim 2, further comprising the delivery of the $AT_4$ receptor ligand locally.

4. The method of inhibiting angiogenesis according to claim 1 or claim 2, further comprising the delivery of the $AT_4$ receptor ligand intravascularly.

5. The method of inhibiting angiogenesis according to claim 1 or claim 2, further comprising the delivery of the $AT_4$ receptor ligand intramuscularly.

6. The method of inhibiting angiogenesis according to claim 1 or claim 2, further comprising the delivery of the $AT_4$ receptor ligand intraperitoneally.

7. The method of inhibiting angiogenesis according to claim 1 or claim 2, further comprising the delivery of the $AT_4$ receptor ligand subcutaneously.

8. The method of inhibiting angiogenesis according to claim 1 or claim 2, further comprising the delivery of the $AT_4$ receptor ligand orally.

9. A method of inhibiting the growth and metastasis of solid tumors, comprising the steps of: producing an $AT_4$ receptor ligand, having a structure selected from the group consisting of: $NH_3^+$-norleucine-tyrosine-isoleucine-histidine-$COO^-$(SEQ ID NO: 4), and norleucine-tyrosine-isoleucine-(6-amino-hexanoic acid)-$CONH_2$(SEQ ID NO: 1); and administering the $AT_4$ receptor ligand.

10. A method of inhibiting the growth and metastasis of solid tumors, comprising the steps of: producing an $AT_4$ receptor ligand having a structure of: norleucine-tyrosine-leucine-$\Psi$-$(CH_2$-$NH_2)^{3-4}$-histidine-proline-phenylalanine-$COO^-$(SEQ ID NO: 3; and administering the $AT_4$ receptor ligand.

11. The method of inhibiting the growth and metastasis of solid tumors according to claim 9 or claim 10, further comprising delivery of the $AT_4$ receptor ligand locally.

12. The method of inhibiting the growth and metastasis of solid tumors according to claim 9 or claim 10, further comprising the delivery of the $AT_4$ receptor ligand intravascularly.

13. The method of inhibiting the growth and metastasis of solid tumors according to claim 9 or claim 10, further comprising the delivery of the $AT_4$ receptor ligand intramuscularly.

14. The method of inhibiting the growth and metastasis of solid tumors according to claim 9 or claim 10, further comprising the delivery of the $AT_4$ receptor ligand intraperitoneally.

15. The method of inhibiting the growth and metastasis of solid tumors according to claim 9 or claim 10, further comprising the step of applying the $AT_4$ receptor ligand subcutaneously.

16. The method of inhibiting the growth and metastasis of solid tumors according to claim 9 or claim 10, further comprising the step of applying the $AT_4$ receptor ligand orally.

17. A method of inhibiting the growth and metastasis of breast cancer, comprising the steps of: producing an $AT_4$ receptor ligand, having a structure selected from the group consisting of: $NH_3^+$-norleucine-tyrosine-isoleucine-histidine-$COO^-$(SEQ ID NO: 4), and norleucine-tyrosine-isoleucine-(6-amino-hexanoic acid)-$CONH_2$(SEQ ID NO: 1); and administering the $AT_4$ receptor ligand.

18. A method of inhibiting the growth and metastasis of breast cancer, comprising the steps of: producing an $AT_4$ receptor ligand having a structure of: norleucine-tyrosine-leucine-$\Psi$-$(CH_2$-$NH_2)^{3-4}$-histidine-proline-phenylalanine-$COO^-$(SEQ ID NO: 3); and administering the $AT_4$ receptor ligand.

19. The method of inhibiting the growth and metastasis of breast cancer according to claim 17 or claim 18, further comprising the delivery of the $AT_4$ receptor ligand locally to the tumor.

20. The method of inhibiting the growth and metastasis of breast cancer according to claim 17 or claim 18, further comprising the delivery of the $AT_4$ receptor ligand intravascularly.

21. The method of inhibiting the growth and metastasis of breast cancer according to claim 17 or claim 18, further comprising the delivery of the $AT_4$ receptor ligand intramuscularly.

22. The method of inhibiting the growth and metastasis of breast cancer according to claim 17 or claim 18, further comprising the delivery of the $AT_4$ receptor ligand intraperitoneally.

23. The method of inhibiting the growth and metastasis of breast cancer according to claim 17 or claim 18, further comprising the delivery of the $AT_4$ receptor ligand subcutaneously.

24. The method of inhibiting the growth and metastasis of breast cancer according to claim 17 or claim 18, further comprising the delivery of the $AT_4$ receptor ligand orally.

* * * * *

UNITED STATES PATENT AND TRADEMARK OFFICE
CERTIFICATE OF CORRECTION

| | | |
|---|---|---|
| PATENT NO. | : 7,118,747 B2 | Page 1 of 1 |
| APPLICATION NO. | : 10/675470 | |
| DATED | : October 10, 2006 | |
| INVENTOR(S) | : Joseph W. Harding et al. | |

It is certified that error appears in the above-identified patent and that said Letters Patent is hereby corrected as shown below:

<u>Column 1</u>
Line 5, please add the following new section:

--STATEMENT OF GOVERNMENT INTEREST

This invention was made with government support under Grant No. CA088551 awarded by the National Institutes of Health and DAMD17-0770-448 awarded by the ARMY Medical Research and Material Command. The government may have certain rights in this invention.--

Signed and Sealed this

Fifteenth Day of May, 2007

JON W. DUDAS
*Director of the United States Patent and Trademark Office*

UNITED STATES PATENT AND TRADEMARK OFFICE
CERTIFICATE OF CORRECTION

PATENT NO. : 7,118,747 B2
APPLICATION NO. : 10/675470
DATED : October 10, 2006
INVENTOR(S) : Joseph W. Harding et al.

It is certified that error appears in the above-identified patent and that said Letters Patent is hereby corrected as shown below:

Column 1
Line 5, please add the following new section:

--STATEMENT OF GOVERNMENT INTEREST

This invention was made with government support under Grant No. CA088551 awarded by the National Institutes of Health and DAMD17-0770-448 awarded by the ARMY Medical Research and Material Command. The government has certain rights in the invention.--

This certificate supersedes Certificate of Correction issued May 15, 2007.

Signed and Sealed this

Second Day of October, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,118,747 B2 | Page 1 of 1 |
| APPLICATION NO. | : 10/675470 | |
| DATED | : October 10, 2006 | |
| INVENTOR(S) | : Joseph W. Harding et al. | |

It is certified that error appears in the above-identified patent and that said Letters Patent is hereby corrected as shown below:

<u>Column 1</u>
Line 5, please add the following new section:

--STATEMENT OF GOVERNMENT INTEREST

This invention was made with government support under Grant No. CA088551 awarded by the National Institutes of Health and DAMD17-0110-448 awarded by the ARMY Medical Research and Material Command. The government has certain rights in the invention.--

This certificate supersedes the Certificates of Correction issued May 15, 2007 and October 2, 2007.

Signed and Sealed this

Twenty-ninth Day of January, 2008

JON W. DUDAS
*Director of the United States Patent and Trademark Office*